United States Patent [19]
Sykes et al.

[11] Patent Number: 6,086,873
[45] Date of Patent: Jul. 11, 2000

[54] THERAPEUTIC COMPOSITION AND METHOD OF TREATMENT

[75] Inventors: Thomas R. Sykes; Ragupathy Madiyalakan, both of Edmonton, Canada; Richard P. Baum, Frankfurt, Germany; Antoine A. Noujaim, Edmonton, Canada

[73] Assignee: Altarex, Inc., Edmonton, Canada

[21] Appl. No.: 08/877,511

[22] Filed: Jun. 17, 1997

Related U.S. Application Data

[63] Continuation-in-part of application No. PCT/IB96/00461, May 15, 1996.

[51] Int. Cl.⁷ ................................................. A61K 39/395
[52] U.S. Cl. ..................... 424/130.1; 424/131.1; 424/133.1; 424/138.1; 424/174.1
[58] Field of Search ............................ 424/130.1, 131.1, 424/133.1, 138.1, 174.1

[56] References Cited

U.S. PATENT DOCUMENTS

| | | |
|---|---|---|
| 4,950,480 | 8/1990 | Barber et al. ........................... 424/85.8 |
| 4,997,762 | 3/1991 | Hana, Jr. et al. .................. 435/240.27 |
| 5,053,224 | 10/1991 | Koprowksi ............................. 424/85.8 |
| 5,194,254 | 3/1993 | Barber et al. ........................... 424/85.8 |
| 5,478,556 | 12/1995 | Elliott et al. ............................ 424/852 |

OTHER PUBLICATIONS

Jolliffe Internal Rev. Immunol. vol. 10 p. 241, 1993.
Bhattacharya–Chatterjee et al, Cancer Immunol. Immunther. vol. 38 p. 75, 1994.
Noujaim et al., Current Tumor Diagnosis, 823–829 (1994).
R.P. Baum et al., Cancer, 73: 1121–1125 (1994).
R.P. Baum et al., Hybridoma, 12: 583–589 (1993).
Sykes et al., The Journal of Nuclear Medicine, 36: 1913–1922 (1995).
Kallenbach et al., Curr Stud Hematol Blood Transfus., 70–82 (1989).
Roderick Murray, M.D. et al., J.A.M.A., 8–14 (1955).
S.A. Jose et al., Molecular Immunology, 24: 1145–1150 (1987).
Kristina N. Prodouz et al., Blood, 70: 589–592 (1987).
A. Kleczkowski et al., Photochem. Photobiol., 1: 294–304 (1962).
C.A. Ghiron et al., Photochemistry and Photobiology, 7: 87–92 (1968).
R. Madiyalakan et al., Hybridma, 14: 199–203 (1995).

*Primary Examiner*—Sheela Huff
*Attorney, Agent, or Firm*—Hale and Dorr LLP

[57] ABSTRACT

The present invention is methods and compositions including a photoactivated antibody that is capable of generating or increasing an immune response.

5 Claims, No Drawings

THERAPEUTIC COMPOSITION AND METHOD OF TREATMENT

The present application is a continuation-in-part of pending International application No. PCT/IB96/00461, filed May 15, 1996.

TECHNICAL FIELD

The invention concerns methods and compositions for preparing altered proteins and using the altered proteins to achieve a beneficial result, preferably increasing immunogenicity.

BACKGROUND ART

Ultraviolet (UV) light has a variety of effects on living systems, including whole animals, microorganisms, cells, and their components. Direct exposure of biological materials to UV radiation generally results in alteration of the structure and changes in the physical, chemical, biochemical, and biological properties. The alterations can be subtle to dramatic, and the property changes can be inconsequential to serious (or even fatal). These effects have long been recognized and used advantageously, e.g., in the inactivation of disease-causing viruses.

The prior art teaches that proteins exposed to UV light changes the reactivity of the antibody toward the native protein. The art teaches that the in vivo immunological response to UV-exposed proteins is reduced, due in part to the creation of new antigenic determinants. It is also well known that this change is reflected in the structural components of the binding site between the protein and the antibody. Finally, the art teaches that exposure to UV radiation is a useful method for modifying proteins for conjugation purposes, but the immunological implications of such a procedure are not addressed.

The fundamental ultraviolet (UV) photoactivation processes, for enhanced immunogenicity purposes, are governed by two major categories of factors which affect the potential photochemical reactions of the target molecules. The first category relates to the nature of the UV source including the emission wavelength spectra: the duration of exposure; the overall intensity of exposure as determined by the UV source (with or without filters) characteristics (power, number of units, age, etc.), the geometry of exposure (configuration, volume, distance, reflection, adsorption, etc.) of the system and the properties of the target sample container (composition, thickness, optical properties). These parameters define the intensity and energy of incident UV exposure.

The second category of factors relates to the nature of the exposed matrix including the media components (solution additives type, concentration, pH, etc. in relation to their photochemical and chemical properties). These define the nature of the absorbing matrix in which the photoactivation process takes place. External factors such as temperature and its control may also play a role.

Given this multitude of parameters, it is very often difficult to compare conditions from different systems to one another. One estimator of comparability is energy incident on the target solution interface over the duration of exposure and expressed as Joules (J) per square centimeter ($cm^2$). Our exposure conditions are typically estimated to be 9 $J/cm^2$ and we anticipate effective exposures would lie in the range of 0.01–1000 $J/cm^2$ given the other potential considerations mentioned above.

All vertebrates have an immune system. The ability of vertebrates to protect themselves against infectious microbes, toxins, viruses, or other foreign macromolecules is referred to as immunity. Immunity is highly specific and is a fundamental characteristic of immune responses. Many of the responses of the immune system initiate the destruction and elimination of invading organisms and any toxic molecules produced by them. Because the nature of these immune reactions is inherently destructive, it is essential that the response is precisely limited to the foreign molecules and not to those of the host itself. This ability to distinguish between foreign molecules and self molecules is another fundamental feature of the immune system.

Acquired or specific immunity comprises defense mechanisms which are induced or stimulated by exposure to foreign substances. The events by which the mechanisms of specific immunity become engaged in the defense against foreign substances are termed immune responses. Vertebrates have two broad classes of immune responses: antibody responses, or humoral immunity, and cell-mediated immune responses, or cellular immunity. Humoral immunity is provided by B lymphocytes, which, after proliferation and differentiation, produce antibodies (proteins also known as immunoglobulins) that circulate in the blood and lymphatic fluid. These antibodies specifically bind to the antigen that induced them. Binding by antibody inactivates the foreign substance, e.g., a virus, by blocking the substance's ability to bind to receptors on a target cell. The humoral response primarily defends against the extracellular phases of bacterial and viral infections. In humoral immunity, serum alone can transfer the response, and the effectors of the response are soluble protein molecules called antibodies.

The second class of immune responses, cellular immunity, involve the production of specialized cells, e.g., T lymphocytes, that react with foreign antigens on the surface of other host cells. The cellular immune response is particularly effective against fungi, parasites, intracellular viral infections, cancer cells and other foreign matter. In fact, the majority of T lymphocytes play a regulatory role in immunity, acting either to enhance or suppress the responses of other white blood cells. These cells, called helper T cells and suppressor T cells, respectively, are collectively referred to as regulatory cells. Other T lymphocytes, called cytotoxic T cells, kill virus-infected cells. Both cytotoxic T cells and B lymphocytes are involved directly in defense against infection and are collectively referred to as effector cells.

The immune system has evolved so that it is able to recognize surface features of macromolecules that are not normal constituents of the host. As noted above, a foreign molecule which is recognized by the immune system (i.e., bound by antibodies), regardless of whether it can itself elicit a response is called an "antigen", and the portion of the antigen to which an antibody binds is called the "antigenic determinant", or "epitope". Some antigens, e.g., tumor-associated antigens such as ovarian cancer or breast cancer antigens, have multiple antibody binding sites. Because of the highly specific nature of the antibody-antigen bond, a primary means of distinguishing between antigens, or between different epitopes on the same antigen, is by antibody binding properties, e.g., the antigen binding site and the strength of the bond.

The conventional definition of an antigen is a molecule that can elicit in a vertebrate host the formation of a specific antibody or the generation of a specific population of lymphocytes reactive with the molecule. As frequently occurs in science, however, it is now known that this definition, although accurate, is not complete. For example, it is now known that some disease conditions suppress or inactivate the host immune response. Under these conditions, a tumor antigen does not elicit an antibody or generate specific lymphocytes. Thus, not all antigens are capable of eliciting a human immune response.

The failure in the definition centers on a two-part aspect of the immune response: the first step in the immune response is the recognition of the presence of a foreign entity; the second step is a complex array or cascade of reactions, i.e., the response. In the tumor antigen example given above, the immune system can recognize the presence of a foreign antigen, but it cannot respond. In another example, a failure in the immune system's ability to distinguish between self and non-self appears to be at the origin of many autoimmune diseases. Again, this is a failure in recognition, not response.

As used herein, therefore, if an antigen can be recognized by the immune system, it is said to be antigenic. If the immune system can also mount an active response against the antigen, it is said to be immunogenic. Antigens which are immunogenic are usually macromolecules (such as proteins, nucleic acids, carbohydrates and lipids) of at least 5000 Daltons molecular weight. Smaller non-immunogenic molecules, e.g., haptens and small antigenic molecules, can stimulate an immune response if associated with a carrier molecule of sufficient size.

Antibodies, also known as immunoglobulins, are proteins. They have two principal functions. The first is to recognize (bind) foreign antigens. The second is to mobilize other elements of the immune system to destroy the foreign entity.

The antigen recognition structures of an antibody are variable domains, and are responsible for antigen binding. The immune system mobilization structures, the second function of the antibody, are constant domains; these regions are charged with the various effector functions: stimulation of B cells to undergo proliferation and differentiation, activation of the complement cell lysis system, opsonization, attraction of macrophages to ingest the invader, etc. Antibodies of different isotypes have different constant domains and therefore have different effector functions. The best studied isotypes are IgG and IgM.

The antibody itself is an oligomeric molecule, classified, according to its structure, into a class (e.g., IgG) and subclass (e.g., IgG1). IgG molecules are the most important component of the humoral immune response and are composed of two heavy (long) and two light (short) chains, joined by disulfide bonds into a "Y" configuration. The molecule has two variable regions (at the arms of the "Y"). The regions are so named because antibodies of a particular subclass, produced by a particular individual in response to different antigens, will differ in the variable region but not in the constant regions. The variable regions themselves are composed of both a relatively invariant framework, and of hypervariable loops, which confer on the antibody its specificity for a particular epitope. An antibody binds to an epitope of an antigen as a result of molecular complementarity. The portions of the antibody which participate directly in the interaction is called "antigen binding site", or "paratope". The antigens bound by a particular antibody are called its "cognate antigens".

An antibody of one animal will be seen as a foreign antigen by the immune system of another animal, and will therefore elicit an immune response. Some of the resulting antibodies will be specific for the unique epitopes (idiotype) of the variable region of the immunizing antibody, and are therefore termed anti-idiotypic antibodies. These often have immunological characteristics similar to those of an antigen cognate to the immunizing antibody. Anti-isotypic antibodies, on the other hand, bind epitopes in the constant region of the immunizing antigen.

The binding of an antigen to an antibody is reversible. It is mediated by the sum of many relatively weak non-covalent forces, including hydrophobic and hydrogen bonds, van der Waals forces, and ionic interactions. These weak forces are effective only when the antigen molecule is close enough to allow some of its atoms to fit into complementary recesses on the surface of the antibody. The complementary regions of a four-chain antibody unit are its two identical antigen-binding sites; the corresponding region on the antigen is an antigenic determinant. Many antigenic macromolecules have many different antigenic determinants.

Three classes of immunotherapy are currently under investigation: 1) passive immunotherapy; 2) active immunotherapy with antigens; and 3) active immunotherapy with antibodies. Unfortunately, each has met with limited success. Immunotherapy, however, is preferred over antiproliferative chemotherapeutic agents, such as pyrimidine or purine analogs, in certain stages of cancer. The analogs compete with pyrimidine and purine as building blocks used during a cell's growth cycle. The analogs are ineffective where growth is non-cycling or dormant. The majority of micrometastatic cells appear to be non-cycling or dormant. The cytotoxic effect of immunotherapy operates independently of cell cycle.

"Passive immunotherapy" involves the administration of antibodies to a patient. Antibody therapy is conventionally characterized as passive since the patient is not the source of the antibodies. However, the term passive is misleading because the patient can produce anti-idiotypic secondary antibodies which in turn can provoke an immune response which is cross-reactive with the original antigen. "Active immunotherapy" is the administration of an antigen, in the form of a vaccine, to a patient, so as to elicit a protective immune response. Genetically modified tumor cell vaccines transfected with genes expressing cytokines and co-stimulatory molecules have also been used to alleviate the inadequacy of the tumor specific immune response.

The administration to humans of mouse antibodies, because they are recognized as "foreign," can provoke a human anti-mouse antibody response ("HAMA") directed against mouse-specific and mouse isotype-specific portions of the primary antibody molecule. This immune reaction occurs because of differences in the primary amino acid sequences in the constant regions of the immunoglobulins of mice and humans. Both IgG and IgM subclasses of HAMA have been detected. The IgG response appears later, is longer-lived than the typical IgM response, and is more resistant to removal by plasmapheresis.

Clinically, however, HAMA: 1) increases the risk of anaphylactic or serum sickness-like reactions to subsequent administration of mouse antibodies; 2) can interfere with the immunotherapeutic effect of subsequently injected mouse antibodies by complexing with those antibodies, increasing clearance from the body, reducing tumor localization, enhancing uptake into the liver and spleen, and/or hiding the tumor from therapeutic agents; and 3) can interfere with immunodiagnostic agents and thereby hinder monitoring of the progress of the disease and course of treatment.

Various clinical trials have used antibodies as therapeutic agents against solid tumors. No consistent pattern of response or improved survival has yet emerged. By contrast, antibody therapy has more often induced complete and long-lasting remissions in B-cell or T-cell lymphomas or leukemias. Explanations for solid tumor failures include antigenic heterogeneity and insufficient accessibility of epithelial cells to the injected antibodies as well as to secondary effector molecules like complement or effector cells.

If a specific antibody from one animal is injected as an immunogen into a suitable second animal, the injected antibody will elicit an immune response (e.g., produced antibodies against the injected antibodies—"anti-antibodies"). Some of these anti-antibodies will be specific for the unique epitopes (idiotopes) of the variable domain of the injected antibodies. These epitopes are known collectively as the idiotype of the primary antibody; the secondary (anti-) antibodies which bind to these epitopes are known as anti-idiotypic antibodies. The sum of all idiotopes present on the variable portion of an antibody is referred to as its idiotype. Idiotypes are serologically defined, since injection of a primary antibody that binds an epitope of the antigen may induce the production of anti-idiotypic antibodies. When binding between the primary antibody and an anti-idiotypic antibody is inhibited by the antigen to which the primary antibody is directed, the idiotype is binding site or epitope related. Other secondary antibodies will be specific for the epitopes of the constant domains of the injected antibodies and hence are known as anti-isotypic antibodies. As used herein, anti-idiotype, anti-idiotypic antibody, epitope, or epitopic are used in their art-recognized sense.

The "network" theory states that antibodies produced initially during an immune response will carry unique new epitopes to which the organism is not tolerant, and therefore will elicit production of secondary antibodies (Ab2) directed against the idiotypes of the primary antibodies (Ab1). These secondary antibodies likewise will have an idiotype which will induce production of tertiary antibodies (Ab3) and so forth.

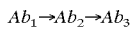

$Ab_1 \rightarrow Ab_2 \rightarrow Ab_3$

The network theory also suggests that some of these secondary antibodies (Ab2) will have a binding site that is the complement of the complement of the original antigen and thus will reproduce the "internal image" of the original antigen. In other words, an anti-idiotypic antibody may be a surrogate antigen.

A traditional approach to cancer immunotherapy has been to administer anti-tumor antibodies, i.e., antibodies which recognize an epitope on a tumor cell, to patients. However, the development of the "network" theory led investigators to suggest the direct administration of exogenously produced anti-idiotype antibodies, that is, antibodies raised against the idiotype of an anti-tumor antibody. Such an approach is disclosed in U.S. Pat. No. 5,053,224 (Koprowski, et al.). Koprowski assumes that the patient's body will produce anti-antibodies that will not only recognize these anti-idiotype antibodies, but also the original tumor epitope.

There are four major types of anti-idiotypic antibodies. The alpha-type binds an epitope remote from the paratope of the primary antibody. The beta-type is one whose paratope always mimics the epitope of the original antigen. The gamma-type binds near enough to the paratope of the primary antibody to interfere with antigen binding. The epsilon-type recognizes an idiotypic determinant that mimics a constant domain antigenic structure.

Two therapeutic applications arose from the network theory: 1) administer Ab1 which acts as an antigen inducing Ab2 production by the host; and 2) administer Ab2 which functionally imitates the tumor antigen.

Active immunization of ovarian cancer patients with repeated intravenous applications of the F(Ab')$_2$ fragments of the monoclonal antibody OC125 was reported to induce remarkable anti-idiotypic antibody (Ab2) responses in some of the patients. Preliminary results suggested that patients with high Ab2 serum concentrations had better survival rates compared to those where low or no Ab2 serum levels were detected. See Wagner, U. et al., "Clinical Course of Patients with Ovarian Carcinomas After Induction of Anti-idiotypic Antibodies Against a Tumor-Associated Antigen," Tumor Diagnostic & Therapie, 11:1–4, (1990).

A human anti-idiotypic monoclonal antibody (Ab2) has been shown to induce anti-tumor cellular responses in animals and appears to prolong survival in patients with metastatic colorectal cancer. See Durrant, L. G. et al., "Enhanced Cell-Mediated Tumor Killing in Patients Immunized with Human Monoclonal Anti-Idiotypic Antibody 105AD7, " Cancer Research, 54:4837–4840 (1994). The use of anti-idiotypic antibodies (Ab2) for immunotherapy of cancer is also reviewed by Bhattacharya-Chatterje, et al; Cancer Immunol Immunother. 38:75–82 (1994).

SUMMARY OF THE INVENTION

Much of the art has focused on reducing the immunological response to an injected antibody for the obvious reason of reducing the host's ability to lessen or counteract a therapeutically beneficial antibody. PCT Application No. PCT/IB96/00461 focused on using the injected antibody to trick the host's immune system into generating a response against a previously unrecognized antigen. It is also known in the art to focus on mechanisms for preparing the antibody itself. For example, it is well known to expose an antibody to UV light to enhance it's conjugation characteristics concomitantly with reducing its isotypic immunogenicity or immunogenicity to the constant portion of the antibody (i.e., the F$_c$ portion) (see, for example, PCT Application No. PCT/CA93/00110).

In contrast, the present invention is directed to preparing antibodies using UV light so that the immunogenicity of the whole antibody is increased. As used herein, increasing the immunogenicity refers to increasing the recognition and/or response of an anti-idiotypic and/or anti-isotypic antibody.

In accordance with the present invention, it is beneficial to generate an enhanced response in order to produce a therapeutic benefit. For example, in accordance with the present invention, it may be desirable to administer UV-exposed antibodies to a cancer patient, with the specific purpose of generating an immune response (i.e., producing anti-idiotypic antibodies) to the UV-exposed antibody. This response may provide a therapeutic advantage via the humoral and cellular consequences directed to the cancer cells. In accordance with one aspect of the invention, the UV-exposed protein exhibits increased immunogenicity and therefore may be useful as a therapeutic for a disease.

The process of the present invention results in heretofore unreported changes, not to the biological function of a binding reagent such as an antibody to bind antigen, but rather to its ability to act as an immunogen. As previously suggested, photoactivation results in disulfide cleavage with sulphydryl generation which is useful for conjugation purposes, while other uses of UV exposure of this type suggest reduced immunogenicity results (Kieczkowski et al. 1962, Deag et al 1995). In contrast, the protein alteration processes of the present invention result in a modified protein with enhanced immunogenic potential. Perhaps the hydrophobicity/hydrophilicity has been altered by minor tryptophan disruption in combination with sulphydryl generation to enhance its recognition/response by the immune cells. It is further possible that the antibody's constant portion has key amino acid specific changes which enhance Fc-mediated antigen presenting cell recognition. This is not related to changes in the polymeric state of the protein whereby aggregated forms (as have been observed for human immunoglobulins after UV exposure) are directed to phagocytic cells, since our photoactivated product maintains its monomeric state. The final extent of presentation and response of the antibody/antigen complex also improved as a result of photoactivation as detected by the HAMA response of antigen-positive patients injected with the antibody.

DISCLOSURE OF THE INVENTION

The present invention involves preparing a protein so that its immunogenicity is increased by exposing the protein to UV radiation. The invention also comprises administering the UV-exposed protein to a patient in order to achieve a pre-determined therapeutic effect.

The protein, preferably an antibody, may be directed against any antigen of clinical significance, but preferably is directed against a tumor-associated antigen (TAA). In the case of TAA, the cancer may include, but is not limited to lung, colon, rectum, breast, ovary, prostate gland, head, neck, bone, immune system, or any other anatomical location. The subject may be a human or animal subject. Illustrative tumors and tumor markers are listed U.S. Pat. No. 5,075,218.

The methods of the present invention involve any cancer that produces a soluble multi-epitopic TAA. As used herein soluble is used to describe any antigen that is detectable in a body fluid, i.e., blood, serum, ascites, saliva, or the like. In accordance with the present invention, the preferred tumors are those that: shed soluble tumor antigens, e.g., tumor antigens shed into the bloodstream, as opposed to a surface antigen or an intracellular antigen; exhibit a multi-epitopic tumor associated antigen, preferably of carbohydrate or glycoprotein (e.g., mucin) nature; and can be found at a concentration in the patient's body fluid more than is normally present in healthy controls and such a high level signifies a poor prognosis for the patient, yet has not initiated an immune response. As is well known by one skilled in the art, one method of determining whether the concentration of the TAA is greater than is predictive of recurrence of the disease is by comparing the patient's concentration to that of a healthy control. If the concentration of the TAA is higher than the healthy control, then the patient's concentration is predictive of poor prognosis of the disease.

A protein as used herein, refers to one member of an immunologic pair, e.g., a binding moiety that is capable of binding to a single epitope expressed on the tumor antigen. Exemplary binding agents include, but are not limited to: monoclonal antibodies ("MAb"); chimeric monoclonal antibodies ("C-MAb"); genetically engineered monoclonal antibodies ("G-MAb"); fragments of monoclonal antibodies (including but not limited to "F(Ab)$_2$", "F(Ab)" and "Dab"); single chains representing the reactive portion of monoclonal antibodies ("SC-MAb"); tumor-binding peptides; any of the above joined to a molecule that mediates an effector function; and mimics of any of the above. The antibody may be a polyclonal antibody or a monoclonal antibody. When the subject is a human subject, the antibody may be obtained by immunizing any animal capable of mounting a usable immune response to the antigen, such as a mouse, rat, goat sheep, rabbit or other suitable experimental animal. In the case of a monoclonal antibody, antibody producing cells of the immunized animal may be fused with "immortal" or "immortalized" human or animal cells to obtain a hybridoma which produces the antibody. If desired, the genes encoding one or more of the immunoglobulin chains may be cloned so that the antibody may be produced in different host cells, and if desired, the genes may be mutated so as to alter the sequence and hence the immunological characteristics of the antibody produced. Fragments, or fragments of binding agents, may be obtained by conventional techniques, such as by proteolytic digestion of the binding agent using pepsin, papain, or the like; or by recombinant DNA techniques in which DNA encoding the desired fragment is cloned and expressed in a variety of hosts. Irradiating any of the foregoing entities, e.g., by ultraviolet light will enhance the immune response to a multi-epitopic antigen under similar conditions. In a preferred embodiment of the invention, effector functions that mediate CDC or ADCC are not required.

In an embodiment of the invention, a suitable composition for an ovarian tumor associated antigen contains an altered protein that binds the CA 125 antigen. In another embodiment of the invention, a suitable composition for gastrointestinal cancer contains a binding agent that binds the CA 19.9 antigen. In yet another embodiment of the invention, a suitable composition for breast cancer contains a binding agent that binds the CA 15.3 antigen. Various binding agents, antibodies, antigens, and methods for preparing, isolating, and using the antibodies are described in U.S. Pat. No. 4,471,057 (Koprowski) and U.S. Pat. No. 5,075,218 (Jette, et al.), both incorporated herein by reference. Furthermore, many of these antibodies are commercially available from Centocor, Abbott Laboratories, Commissariat a L'Energie Atomique, Hoffman-LaRoche, Inc., Sorin Biomedica, and FujiRebio.

In accordance with the present invention, an antibody is photoactivated for the purpose of eliciting an immune response by exposing the antibody to radiation, wherein the resulting altered antibody is capable of generating an immune response when administered to an animal typically capable of generating an immune response to the native form of the antibody. In a preferred embodiment of the invention, the antibody is exposed to ultraviolet light. In a most preferred embodiment, the antibody is exposed to ultraviolet light at a wavelength from about 200 nm to about 400 nm, at from about 0.1 to about 1000 Joules/cm$^2$, for from about 1 to about 180 minutes (more preferably, about 10 to about 30 minutes).

Any composition that includes an altered protein according to the invention may be used to initiate an in vivo immune response. The composition may include one or more adjuvants, one or more carriers, one or more excipients, one or more stabilizers, one or more imaging reagents, and/or physiologically acceptable saline. Generally, adjuvants are substances mixed with an immunogen in order to elicit a more marked immune response. Control vaccinations without the adjuvant resulted in humoral immune responses. The composition may also include pharmaceutically acceptable carriers. Pharmaceutically accepted carriers include but are not limited to saline, sterile water, phosphate buffered saline, and the like. Other buffering agents, dispersing agents, and inert non-toxic substances suitable for delivery to a patient may be included in the compositions of the present invention. The compositions may be solutions suitable for administration, and are typically sterile and free of undesirable particulate matter. The compositions may be sterilized by conventional sterilization techniques. In a preferred embodiment of the invention, the composition includes photoactivated antibody in phosphate buffered saline or pyrophosphate buffered saline, at a pH from about 5 to about 10.

In accordance with a method of the invention, the altered protein may be administered to the patient by any immunologically suitable route. For example, the composition containing the altered protein may be introduced into the patient by an intravenous, subcutaneous, intraperitoneal, intradermal, intramuscular, or intralymphatic routes, in solution, tablet, or aerosol form. Liposomes, biodegradable microspheres, micelles, or the like may also be used as a carrier, vehicle, or delivery system. Furthermore, using ex vivo procedures well known in the art, blood or serum from the patient may be removed from the patient; optionally, it may be desirable to purify the antigen in the patient's blood; the blood or serum may then be mixed with a composition that includes a binding agent according to the invention; and the treated blood or serum is returned to the patient. The clinician may compare the anti-idiotypic and anti-isotypic responses associated with these different routes in determining the most effective route of administration. The invention should not be limited to any particular method of introducing the protein into the patient.

Dosage

In accordance with the methods of the present invention, a composition comprising the altered protein may be administered in an amount sufficient to recognize and bind the pre-determined tumor associated antigen. In a preferred embodiment of the invention, the dosage is sufficient to generate or elicit an immune response against the TAA. An immunologically or therapeutically effective or acceptable amount of binding agent is an amount sufficient to bind a pre-determined antigen in vivo or ex vivo, and is capable of eliciting an immune response to the antigen. The response inhibits or kills tumor cells that carry and present a newly accessible epitope, thereby ameliorating or eliminating the disease or condition that produces the antigen. The immune response may take the form of a humoral response, a cell-mediated response, or both. In a preferred embodiment of the invention, the dosage of the monoclonal antibody is less than the dosage required to elicit ADCC or CDC.

The concentration or dosage of the protein in the composition can vary widely, e.g., from less than about 0.01% to about 15 to 20% by weight. As noted above, the composition is administered in an amount sufficient to stimulate an immune response against the antigen. Amounts effective for this use will depend in part on the severity of the disease and the status of the patient's immune system. Generally, the composition will include about 0.1 $\mu$g to about 2 mg or more of protein agent per kilogram of body weight, more commonly dosages of about 1 $\mu$g to about 200 $\mu$g per kilogram of body weight. The concentration will usually be at least 0.5%; any amount may be selected primarily based on fluid volume, viscosity, antigenicity, etc., in accordance with the particular mode of administration.

Administration may be more than once, preferably three times over a prolonged period. As the compositions of this invention may be used for patient's in a serious disease state, i.e., life-threatening or potentially life-threatening, excesses of the binding agent may be administered if desirable. Actual methods and protocols for administering pharmaceutical compositions, including dilution techniques for injections of the present compositions, are well known or will be apparent to one skilled in the art. Some of these methods and protocols are described in *Remington's Pharmaceutical Science*, Mack Publishing Co. (1982). Administration may also include ex vivo administration protocols, e.g., removing a portion of a patient's body fluid, contacting in vitro the body fluid with the therapeutic composition, and then returning the treated body fluid to the patient.

A binding agent may be administered in combination with other binding agents, or may be administered in combination with other treatment protocols or agents, e.g., chemotherapeutic agents.

The effectiveness of the proteins of the present invention may be monitored in vitro or in vivo. Humoral responses may be monitored in vitro by conventional immunoassays, where the anti-tumor activity of the response may be determined by complement-mediated cellular cytotoxicity and/or antibody-dependent cellular cytotoxicity (ADCC) assays. The assay methodologies are well know, and are described in *Handbook of Experimental Immunology*, Vol. 2, Blackwell Scientific Publications, Oxford (1986). Other assays may be directed to determining the level of the antigen in the patient or tissue. Cell-mediated immunity may be monitored in vivo by the development of delayed-type hypersensitivity reactions, or other in vivo or in vitro means known to those skilled in the art, including but not limited to the skin test reaction protocol, lymphocyte stimulation assays, measuring the toxicity of a subject's lymphocytes to tumor cells by using a standard radioactive release assay, by a limiting dilution assay, or by measuring plasma levels of IL-2 using standard ELISA assays.

EXAMPLES

Example 1

Rat Study

Normal, healthy, Sprague-Dawley rats were used. Animals were randomly grouped (4 per group) to receive four different doses (5 $\mu$g, 10 Figure, 25 $\mu$g and 50 $\mu$g) of two preparations. Pre-injection blood samples were drawn prior to initiation of the injection schedule. Each rat received the appropriate dose of MAb diluted in sterile 0.01 M phosphate buffered saline intravenously. A second study group received 20 $\mu$ of each MAb preparation with or without Incomplete Freund's Adjuvant (IFA). Blood samples were taken just prior to the dose injection at 0, 21, 42, 63 and 77 days.

MAb-B43.13 is a murine IgG, reactive with CA 125. Antibody preparations consisted of MAb-B43.13 in the native form or in a UV-exposed form (e.g., photoactivated). Native MAb was diluted from a stock concentration of 5 mg/mL with 0.01 M phosphate buffered saline to doses of 5, 10, 25 and 50 $\mu$g/100 $\mu$L. UV exposed MAb was reconstituted from the lyophilized form with 0.01 M phosphate buffered saline (2.2 mg/0.47 mL) and diluted to obtain the same doses as for the native MAb.

An assay was developed to measure the rat anti-mouse response in the serum of the injected animals. Anti-isotype rat anti-mouse antibodies were measured using an ELISA plate coated with an isotype matched control antibody, MOPC 21. Samples were diluted 1/100, allowed to react with the coated antibody, washed, and bound antibody detected using peroxidase conjugated goat anti-rat IgG (H+L) with ABS substrate. Unknowns were read off a standard curve generated using a commercial rat anti-mouse antibody.

The results of the rat anti-mouse (RTAMA) analysis of sera from the various groups of rats injected with native and UV exposed MAb-B43.13 is shown in Table 1 and Table 2. The immunological response to the preparations is expressed in terms of the number of responders in each group, with the numerical cut-off defined in the tables. This value (mean of all pre-injection samples (blanks)+3 S.D.) ensures that a true positive response is measured and the results are unlikely to be due to assay variation. The tabulation of responders is probably more meaningful given that the fluctuation of the magnitude of response can be very large and therefore, hinder interpretation.

TABLE 1

ANIMAL RESPONSE* TO INTRAVENOUS INJECTION OF NATIVE AND UV EXPOSED MAb-B43.13 PREPARATIONS

| Sampling Time | Preparation | Dose ($\mu$g/injection) | | | |
|---|---|---|---|---|---|
| | | 5 | 10 | 25 | 50 |
| Pre-injection (blank) | Native | NA** | NA | NA | NA |
| | UV exposed | NA | NA | NA | NA |
| Day 21 | Native | 0 | 0 | 0 | 0 |
| | UV exposed | 2 | 3 | 1 | 1 |
| Day 42 | Native | 0 | 1 | 0 | 1 |
| | UV exposed | 2 | 3 | 4 | 3 |
| Day 63 | Native | 1 | 3 | 3 | 3 |
| | UV exposed | 2 | 4 | 3 | 4 |
| Day 77 | Native | 2 | 2 | 2 | 1 |
| | UV exposed | 3 | 4 | 4 | 4 |

*Number of animals responding in a group of four (RTAMA values ≧ pre-injection sample mean + 3 S.D.)
**NA = Not Applicable The data tends to confirm that the response to the UV exposed MAb-B43.13 occurs earlier (after only one injection) as shown by the greater number of responders at all dose levels in the Day 21 groups.

Furthermore, at all other time periods (and after multiple injections), the proportional response of each group given intravenous UV exposed MAb-B43.13 is greater. It may be suggested that the response is sustained longer for UV exposed MAb-B43.13 since the native MAb-B43.13 appears to show a reduced response rate from Day 23 to Day 77. Actual values of increased response at day 77 are shown in Table 2.

TABLE 2

TOTAL AND $AB_2$ INDUCTION IN RATS INJECTED WITH NATIVE OR UV-EXPOSED MAB-B43.13

| | TOTAL IMMUNE RESPONSE (mean ± S-E) | $Ab_2$ RESPONSE (mean ± S-E) |
|---|---|---|
| Native Mab-B43.13 | 38.47 ± 2.99* | 18.77 ± 8.23 |
| UV-exposed Mab-B43.13 | 1608.67 ± 369.39* | 87.27 ± 45.11 | n = 3
*p = 0.0496

Example 2

Comparative Analysis

The present invention was compared to the compositions and methods disclosed in PCT Application No. PCT/CA93/00110. The following table shows exemplary distinctions between the various methods and compositions.

TABLE 3A

| PCT/IB96/00461 and PCT/CA93/00110 | Present invention |
|---|---|
| 1. Labeled and unlabeled | 1. Unlabeled |
| 2. Reduced isotypic HAMA and increased idiotypic Ab | 2. Increased total HAMA |
| 3. Independent of the circulating antigen in the serum | 3. Dependent on the serum antigen |
| 4. Structural changes: theoretically SH generation leads to increased immunogenicity | 4. Tryptophan disruption with SH generation leads to increased immunogenicity |

The present invention was also compared to the compositions and methods disclosed in PCT Application No. PCT/IB96/00461. The following Table shows exemplary distinctions between the various methods and compositions.

TABLE 3B

| PCT/IB96/00461 | Present Invention |
|---|---|
| 1. Native antibody | 1. UV-exposed antibody |
| 2. Leads to unique $Ab_3$ production | 2. Leads to $Ab_2$ induction |
| 3. Change in antigen conformation | 3. |
| 4. Exposes previously unrecognized epitope | 4. Forms complex with circulating Antigen; complex is new immunogen |

Example 3

Human Study

The utility of the enhanced immunogenicity of monoclonal antibodies has been demonstrated by the IV injection of UV exposed MAb-B43.13 in over 30 ovarian cancer patients on a compassionate basis in an effort to prolong their survival times. Previous data suggested that MAb-B43.13 could prolong survival in advanced stage ovarian cancer. Each patient received 2 mg of UV exposed MAb-B43.13 and were monitored for their immunological response by assaying serum samples at various time intervals for the formation of human anti-mouse antibodies (HAMA). Table 4 summarizes the HAMA and $Ab_2$ response in these patients.

TABLE 4

| PARAMETER | POSITIVE/TOTAL |
|---|---|
| HAMA | 18/21 |
| $Ab_2$ | 6/21 |
| Number of injections received | 3 |

Therefore this method to enhance the immunological response of the protein by UV exposure, can produce an improved therapeutic agent for the treatment of disease.

Example 4

UV Exposure Conditions For Enhanced Immunogenicity Studies

A typical experimental set-up consists of an eight lamp photoreactor unit (typically 200–400 nm spectra, 90% at 300±20 nm; 3–9 watts/lamp) arranged concentrically about an approximately 15 centimeter diameter cylinder with appropriate associated electronics, shielding, etc. In this photoreactor unit (RMR-600, Southern New England Ultraviolet Company), samples to be exposed are arranged in several configurations: (1) as individual 1.5 ml (borosilicate glass or quartz) vials tubes located on an eight unit carousel (approx. 5 cm diameter) which is rotated in the chamber at 1–5 rpm for 0–180 minutes (typically 30 minutes); (2) as 2 single vial/tubes (as above) placed in the center of the exposure source and exposed for similar time frames; or (3) as a helical glass (as above) coil (approx. 3 mm external diameter) which allows target solution to flow through the photoreactor unit for various time frames of approximately 0–180 minutes, but typically 10–20 minutes. This latter set-up allows considerable volumes of target solution to be exposed on a continuous basis for large-scale manufacturing purposes.

Under any of these exposure conditions, protein target solutions at 0.5–10 mg/ml (typically 5 mg/ml) in a variety of expected benign low molarity buffer solutions (typically phosphate, pyrophosphate, or tartrate; pH 5–10), can be exposed to determine their effects on target protein immunogenicity.

Example 5

Protein Modification As A Result Of UV Exposure

The final chemical species present after photoactivation are specific for a given set of exposure conditions and the composition of the matrix solution (as described above). For simple polypeptides containing any of the three primary UV absorbing (UV-B) amino acids (cystine, tryptophan, tyrosine) the consequences of UV exposure can lead to amide bond cleavage, disulfide bond cleavage, alteration of absorbing amino acids and alteration of adjacent or close proximity amino acids. These changes are brought about by direct photoionization or photoexcitation and indirectly by radical formation from other constituents. The nature and extent of these modifications is highly dependent on the chemical reactivities of the species generated and other constituents reactive tendencies or stabilizing/quenching capabilities. For this size of molecule any alteration generally results in dramatic changes in biological function.

These same reactions can take place in larger proteins, however secondary and tertiary structural elements present differing substrates for UV exposure in spite of similar amino acid sequences. Therefore, the hydrophobic/hydrophilic nature and proximal amino acids from distant chain sequences as a result of folding alter the micro-environment and therefore influence the degree and nature of the modification, in addition to other constituents issues stated above. Given the predominance of the tryptophan absorption profile in this UV band width, it is thought to be the primary site of the initial photoactivation process, but direct action on cysteine and tyrosine are also viable.

The mechanism for indirect amino acid modifications has been proposed as local hydrated electron generation or direct energy transfer from the primary absorbing site. The primary observed changes for large proteins focus on measurable chemical/biochemical changes such as absorption and fluorescence determinations of aromatic amino acids which relate to global modifications. Individual amino acid alterations be detected in this group of proteins where sulphydryl content can be determined as evidence of cysteine disulfide cleavage and/or where a critical amino acid for function is involved. For smaller proteins amino acid hydrolysis and complete quantitation can be performed. The primary concern for functional large proteins, such as enzymes, receptor, or antibodies, is therefore not specific amino acid modification but the consequences of any change on their biological function, and has invariably been described as loss of enzyme function, receptor recognition, or antigen binding.

Example 6

UV Exposed B43-13/CA125 antibody/antigen complex Produces Better CA125 Specific Cellular immune Response and better humoral response.

Better cellular immune response was observed when the UV exposed antibody was presented in association with the antigen to T-cells. Thus, macrophages isolated from mouse peritoneal cavities were stimulated with native B43.13 or UV exposed B43.13 in association with CA125 and presented to CA125 specific mouse T-cells isolated from mice injected with CA125. Control experiments included stimulation of the macrophages without the antigen. When the proliferation of T-cells as monitored by [$^3$H]-thymidine uptake was followed, optimal stimulation index was observed in macrophages stimulated with UV exposed B43.13-CA125 complex.

TABLE 5

| STIMULATING AGENT[1] | STIMULATION INDEX[2] |
|---|---|
| CA125 | 2.76 |
| Native MAb-B43.13 | 3.98 |
| UV-exposed MAb-B43.13 | 3.31 |
| Native MAb-B43.13-CA125 | 4.71 |
| UV-exposed MAb-B43.13-CA125 | 5.28 |

[1]1 μg/ml of the antibody and 100 μ/ml CA125 were used.
[2]Mean of three individual experiments done in triplicate.

Table 6 shows that the humoral response depends on the presence of CA125 present in the patient's sera.

TABLE 6

| CA125 level | $Ab_2$ (# positive/total) |
|---|---|
| <100 μ/ml | 0/4 (0%) |
| >100 μ/ml | 6/16 (38%) |

While the present invention has been described in some detail by way of illustration and example, it should be understood that the invention is susceptible to various modifications and alternative forms, and is not restricted to the specific embodiments set forth. It should be understood that these specific embodiments are not intended to limit the invention, and the intention is to cover all modifications, equivalents, and alternatives falling within the spirit and scope of the invention.

We claim:

1. A method of inducing an immune response in a vertebrate comprising exposing an antibody to ultraviolet light under conditions whereby the ultraviolet light exposes at least one reactive sulfhydryl on the antibody that does not change the biological function of the antibody to bind an antigen, to produce an altered antibody, wherein the altered antibody is unlabeled;

administering the altered antibody to a host capable of generating an immune response to a native form of said antibody;

allowing the host to generate an immune response to the altered antibody, whereby said immune response is greater than the immune response the host would produce against the native antibody.

2. The method of claim 1 wherein generating an immune response to the altered antibody includes generating an immune response to a cancer cell.

3. The method of claim 2 wherein generating an immune response to the altered antibody includes generating anti-idiotypic secondary antibodies that elicit the host's immune response to the cancer cell.

4. The method of claim 2, wherein the cancer cell is ovarian cancer.

5. The method of claim 1 wherein the altered antibody specifically binds to a tumor-associated ovarian cancer antigen.

* * * * *